United States Patent [19]

Motzkau

[11] Patent Number: Plant 6,414

[45] Date of Patent: Nov. 22, 1988

[54] AZALEA PLANT NAMED BOLERO

[75] Inventor: Henry W. Motzkau, Lacey, Wash.

[73] Assignee: Yoder Brothers, Inc., Barberton, Ohio

[21] Appl. No.: 19,305

[22] Filed: Feb. 26, 1987

[51] Int. Cl.[4] ..... A01H 5/00
[52] U.S. Cl. ..... Plt./57
[58] Field of Search ..... Plt./55–57

*Primary Examiner*—James R. Feyrer

*Attorney, Agent, or Firm*—Schwartz, Jeffery, Schwaab, Mack, Blumenthal & Evans

[57] ABSTRACT

An Azalea plant named Bolero, particularly characterized by its evergreen foliage, semi-double hose-in-hose flower form, salmon red flower color, its long lasting flowers, ease of budding, spreading growth habit, mid-season response, profuse and uniform flowering in a year round controlled program, and by its excellent shipping, and cooler tolerance.

1 Drawing Sheet

The present invention comprises a new and distinct cultivar of Azalea plant named Bolero obtained from crossing certain Azalea selections in a program of controlled hybridization by applicant in Lacey, Wash. The seed parent in the breeding program was identified by Code #2118, and the pollen parent by Code #1913.

The new cultivar is similar in many respects to the cultivar Prize, disclosed in U.S. Plant Pat. No. 3,795, having the same characteristics as Prize of:

1. Evergreen foliage.
2. Long lasting flowers.
3. Tolerance to high temperatures.

The new cultivar is distinguished from Prize by the following characteristics:

1. Darker red flower color.
2. Shorter, more spreading growth habit.
3. More cold tolerant.
4. Easier to bud up.

The new cultivar was selected by applicant in Lacey, Wash. from the seedling progeny of the above mentioned parents. Varietal worth was determined by flowering liners from cuttings taken from the initial selection in both a year round and natural season developmental flowering program over a period of 3½ years. Stock growth was evaluated in the vicinity of Southern Florida.

The new cultivar was first asexually reproduced by applicant in Lacey, Wash. by cuttings, and subsequent propagation has taken place at Fort Myers, Fla. Bolero has been found to retain its distinctive characteristics through successive propagations.

When grown in the vicinity of Fort Myers, Fla., Bolero has a response described as mid-season, and the following detailed description is based on observations made of the new cultivar from field grown plants in Fort Myers, Fla. The response time and blooming period may vary significantly with varying environmental conditions such as temperature and amount of daylight. Suggested flowering period is from January 15 through April in a natural season program and all year round in a controlled program.

The accompanying photograph shows in perspective view the unique features of the new cultivar, with colors being as true as possible with color illustrations of this type. Color references are to The Royal Horticultural Society Colour Chart. Where a particular color value is not precise, variations from the closest color value have been noted.

Botanical classification: *Rhododendron hybrida,* evergreen type.

Flower:

*Color.*—Reading location and season: All color readings were taken in an office having cool white florescent fixtures and facing a west window. All readings were taken in October between the hours of 10:00 a.m. and 2:00 p.m. in Fort Myers, Fla. General tonality: Salmon red 51A. Sepals first divide: Lighter than dark red 46A. Petals unfurl: Salmon red 51A. Fully open: Salmon red 51A. Inside of petals: Salmon red 51A. Reverse of petals: Salmon red 51A. Base of petals: Light pink 51D. Outer hose: Salmon red 51A, dispersed with light green 141C. Base of outer hose: Orange pink 38B. Variations: None.

*Bud.*—Size: Medium. Form: Conoidal. Opening habit: Looks somewhat like a rosebud.

*Bloom.*—Size: Medium, average 7.5 cm, range 7–8 cm. Borne: Several together, average 2, range 1–3. Form: Semi-double hose-in-hose.

*Blooming habit.*—Once, profusely. Response: Natural season: Early. Year round: All twelve months.

*Calyx.*—Imperfect hose.

*Peduncle.*—Length: 3 cm. Aspect: Hairy. Strength: Strong.

*Petals.*—Texture: Soft. Substance: Heavy. Appearance: Inside: Satiny. Outside: Satiny. Form: Almost elliptic. Arrangement: Imbricate. Fragrance: None. Persistance: Non shatter. Longevity (keeping quality): Greenhouse: 3 weeks. Home: 4 weeks.

Reproductive organs:

*Stamen-anthers.*—Variable in number from 1–5 per flower. May be petaloid. Immature: Light yellow 5D. Mature: Dark brown 174A.

*Filaments.*—Most have become petaloid, when present very short, purplish red 58B.

*Style.*—Fasciated and branched. Immature: Yellow green 145A. Mature: Greyish brown 164B.

*Stigma.*—Fasciated. Immature: Yellow green 145A. Mature: Orange brown 34D.

*Ovaries.*—Somewhat deformed, flattened, hairy.

Fruit: None.

Foliage:

*Type.*—Evergreen.

*Leaflets.*—Single.

*Size.*—Length: Average, 4.5 cm, range 4.0–4.75 cm. Width: Average, 2.0 cm, range 1.75–2.25 cm. Shape: Oblanceolate. Texture: Dull green, quite hairy. Rib and mid veins: Slightly depressed. Edge: Entire.

*Color (immature foliage).*—Upper surface: Olive green 137C. Lower surface: Lighter than olive green 138B.

*Color (mature foliage).*—Upper surface: Dark green 139A. Lower surface: Olive green 139C.

*Petiole.*—Short, hairy, light green.

Plant (bush):

*Growth habit.*—Semi-upright.

*Breaking habit.*—Good.

*Rooting habit.*—Good.

*Budding ease.*—Good.

*Uniformity of budding.*—Good.

*Growth regulator.*—Required.

*Stems (color).*—Immature wood: Yellow green 144B. Mature wood: Brown 165B.

*Responsiveness to day length and temperature.*—Buds easily and uniformly over a wide range of environmental conditions.

*Resistance to cylindrocladium.*—Good.

*Cooler tolerance.*—Excellent.

*Shipping tolerance.*—Excellent.

I claim:

1. A new and distinct cultivar of Azalea named Bolero, as described and illustrated, and characterized particularly as to novelty by its evergreen foliage, flower form, salmon red flower color, long lasting flowers, ease of budding, spreading growth habit, profuse and uniform flowering in a year round controlled program, and excellent cooler and shipping tolerance.

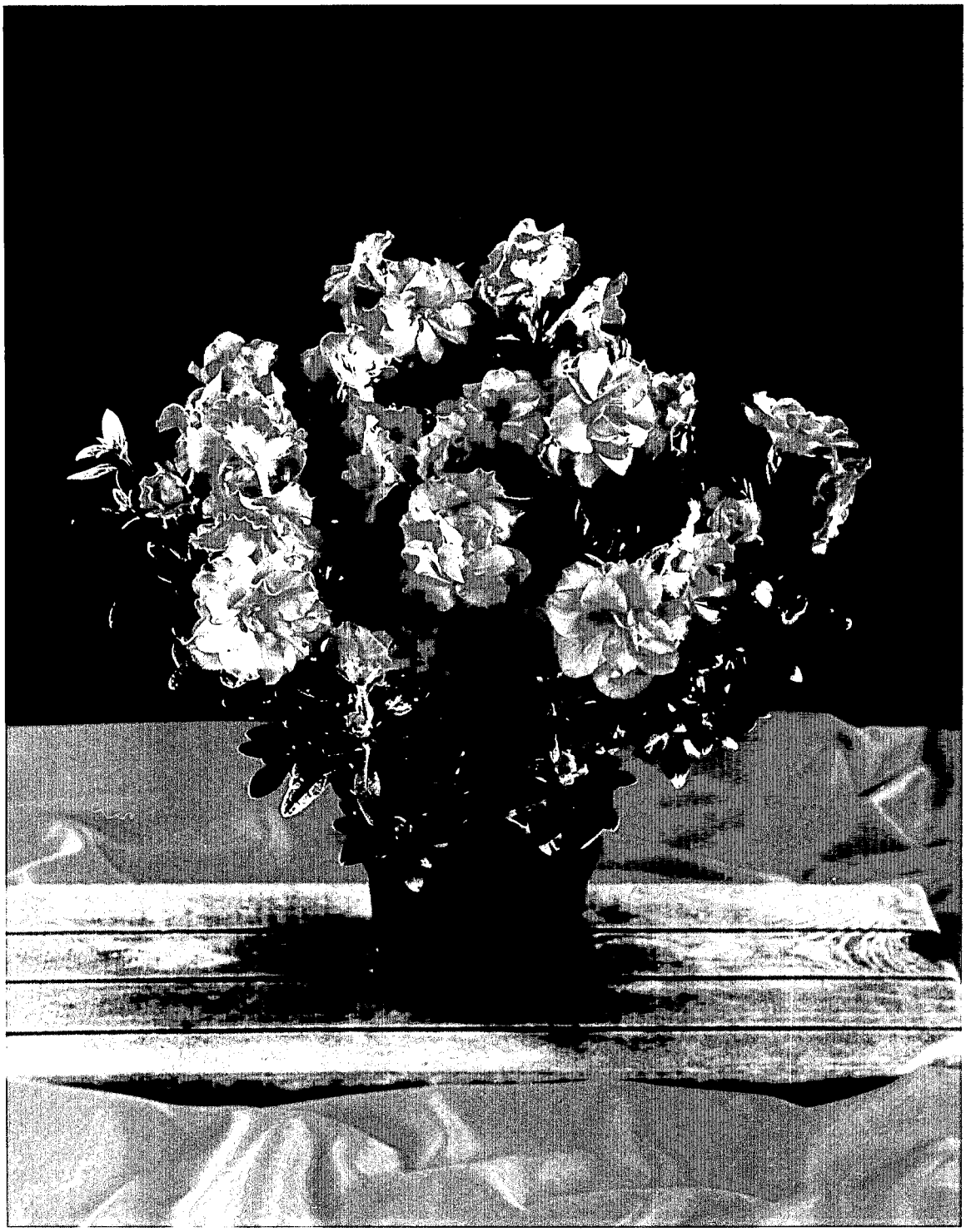

* * * * *